United States Patent [19]
Frank et al.

[11] Patent Number: 5,698,019
[45] Date of Patent: Dec. 16, 1997

[54] LEUCITE-CONTAINING PHOSPHOSILICATE GLASS-CERAMIC

[75] Inventors: Martin Frank, Schaan, Liechtenstein; Marcel Schweiger, Chur, Switzerland; Volker Rheinberger, Vaduz; Wolfram Hoeland, Schaan, both of Liechtenstein

[73] Assignee: Ivoclar AG, Liechtenstein

[21] Appl. No.: 497,722

[22] Filed: Jun. 30, 1995

[30] Foreign Application Priority Data

Jul. 1, 1994 [DE] Germany ............ 44 23 793.6

[51] Int. Cl.$^6$ .................. C03C 10/10; A61C 13/083
[52] U.S. Cl. .................. 106/35; 501/6; 501/10; 501/67; 501/70; 433/212.1; 433/218; 65/33.7
[58] Field of Search .................. 106/35; 501/6, 501/10, 67, 70; 433/212.1, 218; 65/33.7

[56] References Cited

U.S. PATENT DOCUMENTS

| | | | |
|---|---|---|---|
| 3,907,577 | 9/1975 | Kiefer et al. | |
| 4,042,362 | 8/1977 | Mac Dowell et al. | 501/6 |
| 4,604,366 | 8/1986 | Kacicz et al. | 106/35 |
| 4,798,536 | 1/1989 | Katz | 501/6 |
| 5,453,290 | 9/1995 | Van Der Zel | 106/35 |
| 5,466,285 | 11/1995 | Kamiya et al. | 106/35 |

FOREIGN PATENT DOCUMENTS

| | | |
|---|---|---|
| 0 231 773 | 8/1987 | European Pat. Off. |
| 2 558 726 | 8/1985 | France |
| 3306648 | 9/1983 | Germany |
| 242 216 | 1/1987 | Germany |
| 3939831 | 6/1990 | Germany |
| 291 982 | 7/1991 | Germany |
| 4423793 | 2/1996 | Germany |
| 2 199 027 | 6/1988 | United Kingdom |

OTHER PUBLICATIONS

Kokubo, T., "Bioactive Glass Ceramics: Properties and Applications," *Biomaterials*, 12:155–163 (1991) No Month.

*Primary Examiner*—Karl Group
*Attorney, Agent, or Firm*—Nixon, Hargrave, Devans & Doyle

[57] ABSTRACT

A leucite-containing phosphosilicate glass-ceramic is described which, in addition to a leucite crystalline phase and at least one further crystalline phase, also contains one or more glass phases.

15 Claims, No Drawings

LEUCITE-CONTAINING PHOSPHOSILICATE GLASS-CERAMIC

The invention relates to leucite-containing phosphosilicate glass-ceramics and in particular to leucite-containing phosphosilicate glass ceramics which, because of their mechanical, optical, chemical, biological and their processing properties, are suitable in an excellent manner for use in the field of dentistry.

Phosphosilicate glass-ceramics are materials which are constructed mainly from $SiO_2$ and which, alongside other constituents, also contain $P_2O_5$. They have one or more crystalline phases plus one or more glass phases and are obtained from a crystal-free $P_2O_5$-containing silicate starting glass by controlled crystallization.

With leucite-containing glass-ceramics, the controlled crystallization of the starting glass, also called devitrification, leads to the formation of leucite crystals of the $K[AlSi_2O_6]$ type.

Known from the prior art are, firstly, leucite-free phosphosilicate glass-ceramics and, secondly, leucite-containing glass-ceramics and ceramics which are not however derived from the phosphosilicate system.

Leucite-free phosphosilicate glass-ceramics for bone replacement are described for example by Kokubo (*Biomaterials* 12 (1991) 155). They have a MgO—CaO—$SiO_2$ glass matrix with apatite ($Ca_{10}(PO_4)_6O$, $F_2$) and β-wollastonite ($CaO.SiO_2$) crystals homogeneously distributed therein. The glass-ceramics are however bioactive, i.e. they have a particularly high surface reactivity and, upon reaction with body fluids, develop crystals on their surface. This property enables them to form a direct bond, virtually free from connective tissue, with the living bone. In dentistry, for example when using glass-ceramics as a dental crown or bridge, such a bioactive surface reaction is undesirable however.

Further leucite-free bioactive glass-ceramics are known from DE-PS 33 06 648 and DE-OS 39 39 831. These glass-ceramics have mica and apatite as main crystalline phases. A combination of properties such as are important for dental materials and dental products, such as e.g. high strength with simultaneous translucence, is, however, not achievable with these glass ceramics.

Leucite-free glass-ceramics are also known from DD-PS 291 982. They can contain apatite and are usable as a constituent of glass ionomer cements for dentistry. However, disadvantageous features are their low thermal expansion coefficient and their inadequate strength, for which reason they are not suitable as dental restoration material. This is also true of the glass-ceramics described in DD-PS 242 216, which contain mica and cordierite as crystalline phases.

Apart from the mentioned leucite-free glass-ceramics, leucite-containing glass-ceramics are also known, but these contain no phosphorus. Such materials are described for example in U.S. Pat. No. 4,604,366 and U.S. Pat. No. 4,798,536. Even though these glass-ceramics can be processed to give dental crowns, they still have only a low strength and the dental products prepared from them are unsatisfactory as regards their optical and mechanical-biological properties, such as biocompatibility and abrasion resistance.

Finally, phosphate-free leucite-containing glass-ceramics based on feldspar are known from EP-A-0 155 564. By mixing various glass-ceramics, it is possible to establish a desired thermal expansion coefficient.

The object of the invention is to provide glass-ceramics which, in particular as a result of their easy processability, high strength, chemical resistance and their advantageous optical behaviour, can be used as dental materials and dental products moulded from them, such as all-ceramic dental restorations, e.g. crowns, bridges and artificial teeth.

This object is surprisingly achieved by the leucite-containing phosphosilicate glass-ceramic according to claims 1 to 8.

The subject-matter of the present invention is also a process for the preparation of the glass-ceramic, the use of the glass-ceramic as well as moulded dental products which are formed from the glass-ceramic and accordingly contain the glass ceramic.

The leucite-containing phosphosilicate glass-ceramic according to the invention comprises the following components:

| | |
|---|---|
| $SiO_2$ | 49.0 to 57.5% by wt. |
| $Al_2O_3$ | 11.4 to 21.0% by wt. |
| $P_2O_5$ | 0.5 to 5.5% by wt. |
| CaO | 2.5 to 11.5% by wt. |
| $K_2O$ | 9.0 to 22.5% by wt. |
| $Na_2O$ | 1.0 to 9.5% by wt. |
| $Li_2O$ | 0 to 2.5% by wt. |
| $B_2O_3$ | 0 to 2.0% by wt. |
| $TiO_2$ | 0 to 3.0% by wt. |
| $ZrO_2$ | 0.8 to 8.5% by wt. |
| $CeO_2$ | 0 to 3.0% by wt. |
| F | 0.25 to 2.5% by wt. |
| $La_2O_3$ | 0 to 3.0% by wt. |
| ZnO | 0 to 3.0% by wt. |
| BaO | 0 to 3.0% by wt. |
| MgO | 0 to 3.0% by wt. |
| SrO | 0 to 3.0% by wt. | and further comprises a leucite crystalline phase and at least one further crystalline phase plus one or more glass phases. The glass-ceramic preferably consists essentially of the previously mentioned components.

It was found, completely surprisingly, that the controlled crystallization of starting glasses having the chemical composition given above for the glass-ceramic according to the invention results both in the formation of a leucite crystalline phase and in the formation of at least one further crystalline phase, preferably a phosphate-containing crystalline phase. It is assumed that the advantageous properties of the glass-ceramic according to the invention are to be attributed in particular to the simultaneous presence of leucite crystals, which preferably form the main crystalline phase, and further crystals.

Preferred quantity ranges exist for some of the components of the glass-ceramic. These can be chosen independently of one another and are as follows:

| | |
|---|---|
| $SiO_2$ | 50 to 57% by wt. |
| $P_2O_5$ | 0.5 to 4.0% by wt. |
| CaO | 2.5 to 7.0% by wt. |
| $K_2O$ | 9.0 to 15.0% by wt. |
| $Na_2O$ | 5.0 to 9.5% by wt. |
| $Li_2O$ | 0 to 1.5% by wt. |
| $B_2O_3$ | 0 to 1.0% by wt. |
| $TiO_2$ | 0 to 2.5% by wt. |
| $ZrO_2$ | 0.8 to 5.0% by wt. |
| $La_2O_3$ | 0 to 2.0% by wt. |

It is advantageous for the properties of the glass-ceramic and in particular for the mechanical strength if the crystals of the individual phases are essentially of the same size in each case and that the crystals of all crystalline phases have an average size of less than 5 μm, preferably less than 3 μm, relative to the number of crystals.

It has been shown that particularly advantageous glass-ceramics are those in which a leucite crystalline phase and a crystalline phase comprising elongated phosphate-containing crystals are present as crystalline phases. It is quite particularly preferred if the elongated phosphate-containing crystals are needle-shaped apatite crystals which in particular have an average size of less than 2 µm, relative to the number of crystals.

To prepare the glass-ceramic according to the invention, the procedure is that:

(a) a glass is prepared which contains the previously given components, (b) the glass is subjected, in the form of a powder or granulate or of a green compact pressed out of powder, to a heat treatment in the temperature range from 850° to 1200° C. for a period of 30 minutes to 4 hours, in particular 1 to 2.5 hours, with formation of the glass ceramic and (c) an additive is optionally added to the formed glass-ceramic.

In particular, in step (a) the procedure is that suitable starting materials, such as for example oxides, carbonates, phosphates and fluorides, are mixed in the desired weight ratios and melted for 0.5 to 4 hours at a temperature of 1400° to 1700° C., in particular 1500° to 1650° C., to give a homogeneous glass melt. The molten glass is then quenched in water (fritted), as a result of which a granulate is obtained.

The subsequent process step (b) is preferably carried out in such a way that the obtained granulate is dried and ground to a desired particle size. By altering the particle size it is possible to change the properties of the finally formed glass-ceramic. Thus it is possible for example, by using a coarse granulate, to repress the formation of leucite crystals to the benefit of the phosphate-containing crystals. An advantageous average particle size is less than 90 µm and in particular less than 45 µm. The ground glass is then subjected to the already mentioned heat treatment, as a result of which the desired crystalline phases are formed.

It is possible to also add to the glass-ceramic additives such as dyestuffs and fluorescent substances. Suitable dyestuffs are colour pigments, oxides of the 3d elements or metal colloids. Usable fluorescent substances are yttrium silicates doped with d- and/or f-elements.

To change in particular the thermal and optical properties of the glass ceramics, further glasses, ceramics, further glass-ceramics, opacifiers and/or stabilizers can also be added to them as additives.

The microheterogeneous structure of the glass-ceramic according to the invention, i.e. the presence of at least two different crystalline phases and at least one glass phase, was established by means of scanning electron microscopy, and the formed crystals were identified by means of X-ray diffractometry.

In the case of a glass ceramic with two glass phases, as a result of a liquid-liquid phase separation, one glass phase can be present in the form of drops which are embedded in the matrix formed by the other glass phase. Such a demixing is very well detectable by electron microscopy.

The primary or main crystalline phase is preferably formed by leucite crystals. These presumably form during the necessary heat treatment through the mechanism of the controlled surface crystallization at the surface of the individual particles of the starting glass. In the early stage of the crystallization, the leucite crystals are present almost exclusively at the grain boundaries of the individual glass grains, but as the crystallization progresses leucite crystals are also formed inside the glass grains, with the result that these finally are homogeneously distributed over the whole specimen volume. The size distribution of the formed crystals is very narrow.

In addition to the leucite precipitation, at least one further crystalline phase, preferably a phosphate-containing, in particular calcium phosphate-containing, and particularly preferably an apatite-containing crystalline phase, is formed. The apatite can be present e.g. as hydroxyl and/or fluorapatite.

With the help of the X-ray diffractometric examinations, it was possible to show that the phosphate-containing crystalline phase is initially precipitated in spherical form and, as temperature and tempering time increase, crystals having the shape of small rods or needles form. The exact shape of the precipitated crystals depends inter alia on the CaO, $P_2O_5$ and fluorine contents of the starting glass. It has been shown that glass-ceramics in which, in addition to the leucite, phosphate-containing crystals having the shape of small rods or needles are present, have a particularly high mechanical strength.

The given quantity ranges of the components of the glass-ceramic according to the invention are necessary to effect the formation of phosphate-containing crystals having the shape of small rods or needles. It has been shown that, even with low CaO (2.5% by wt.) and $P_2O_5$ (0.5% by wt.) concentrations, in addition to the leucite, a crystalline phase consisting of elongated crystals is present in the structure of the glass-ceramic. However, because of their small size, these crystals are sometimes X-ray amorphous, with the result that it was not possible to determine their identity unequivocally by means of X-ray diffractometry.

Because of the identical shape, however, there is reason to assume that these precipitations are also phosphate-containing crystalline phases.

The crystals contained in the glass-ceramics according to the invention preferably have an average length of at most 3 µm, in particular less than 2 µm, and a diameter of less than 100 nm.

In addition to the aforementioned phases, the glass-ceramics according to the invention can also have further crystalline phases, such as for example $SiO_2$ or $ZrO_2$ crystals.

Because of its outstanding properties, in particular its high strength and chemical resistance, the glass-ceramic according to the invention can be used in advantageous manner as a dental material, such as glass-ceramic cement, or a constituent thereof.

Moulded dental products can also be formed from the glass-ceramic in a simple manner or the glass-ceramic can be used as constituent of such dental products. Preferred moulded dental products are all-ceramic or metal ceramic dental restorations, such as crowns, bridges, part-crowns, inlays, onlays, artificial teeth, stump constructions or facets.

The glass ceramic according to the invention shows particular advantages during processing to give dental restorations which in each case have to be individually adapted for the individual patient, such as e.g. bridges or crowns. It is possible to compress a blank formed from the glass ceramic into the desired shape in the hot viscous state even at temperatures of below 1200° C. Unlike what happens with conventional glass-ceramics, with this treatment there is not even an desired reaction with the investment material, something which is an important advantage for the dental technician.

To prepare moulded dental products, the following procedure in particular can be adopted. Firstly, a powder having a particle size of preferably less than 90 µm is formed from the starting glass or already prepared glass-ceramic according to the invention. This powder is uniaxially dry-pressed at room temperature and then sintered together at a temperature of 850° to 1200° C., preferably 900° to 1000° C., for 15 minutes to 2 hours, preferably 30 minutes to 1 hour. The glass-ceramic blank obtained in this way is then pressed into a hollow mould in a special pressing oven, such as is known for example from EP-A-0 231 773, at temperatures up to 1200° C., preferably of 950° up to 1150° C. This process is also called "viscous flow". The mould represents the desired dental suprastructure, such as crown, part-crown or bridge. After cooling and removal from the mould, the desired finished dental product is obtained.

The dental products according to the invention can also still be subjected to a thermal post-treatment after they have been prepared and/or provided with an additional glaze, sintered ceramic or glass-ceramic layer. These additional treatments are usually carried out at a temperature of 700° to 1000° C. A particularly high strength is achieved if the glass-ceramic is initially subjected to a thermal additional treatment to develop an intrinsic glaze and is then provided with a further glaze or glass-ceramic layer. The thus-obtained dental products according to the invention have translucent properties and flexural strengths of up to 400 MPa.

Moulded dental products can also be prepared by milling from the monolithic glass-ceramic ingot.

Finally, the glass-ceramics according to the invention can also be mixed in powder form with e.g. water and applied on a metal or ceramic substrate, whereby after moulding and baking at temperatures of 700° to 1100° C. a finished dental restoration, such as e.g. a bridge, a crown, a part-crown, a facet, a stump construction or an artificial tooth for removable prostheses, results.

To sum up, because of their advantageous mechanical, optical, chemical and biological properties and their processing properties, the glass-ceramics according to the invention are particularly suitable in dentistry, e.g. for the preparation of dental restorations.

The invention is explained in more detail below with reference to examples.

EXAMPLES

Examples 1 to 29

In total, 29 different glass-ceramics according to the invention were prepared. They had the chemical compositions given in Table 1.

Given in Table II for some of these glass-ceramics are the heat treatment method used in each case and any additional treatments as well as selected properties.

The examples illustrate how, by altering the chemical composition of the starting glass and the preparation process, glass-ceramics with different structure and properties can be obtained.

TABLE I

Chemical composition of preferred glass ceramics according to the invention (data in % by wt.)

| Example No. | $SiO_2$ | $Al_2O_3$ | $P_2O_5$ | CaO | $K_2O$ | $Na_2O$ | $Li_2O$ | $B_2O_3$ | $TiO_2$ | $ZrO_2$ | $CeO_2$ | F | $La_2O_3$ | SrO | MgO | BaO | ZnO |
|---|---|---|---|---|---|---|---|---|---|---|---|---|---|---|---|---|---|
| 1 | 54.2 | 15.2 | 2.6 | 5.6 | 10.7 | 9.3 | | | 0.3 | 1.8 | | 0.3 | | | | | |
| 2 | 50.1 | 14.5 | 4.5 | 5.3 | 22.1 | 1.0 | | | 0.3 | 1.7 | | 0.5 | | | | | |
| 3 | 49.0 | 14.3 | 4.4 | 5.2 | 21.6 | 1.0 | | 2.0 | 0.3 | 1.7 | | 0.5 | | | | | |
| 4 | 49.6 | 11.5 | 4.5 | 5.3 | 16.7 | 4.4 | | | 0.3 | 4.3 | | 0.5 | 2.9 | | | | |
| 5 | 55.7 | 15.2 | 2.5 | 5.0 | 14.0 | 5.0 | | | 0.3 | 1.8 | | 0.5 | | | | | |
| 6 | 50.3 | 15.5 | 2.5 | 3.6 | 13.3 | 7.0 | | | 2.3 | 4.3 | 0.9 | 0.3 | | | | | |
| 7 | 55.8 | 11.4 | 2.5 | 4.3 | 12.3 | 7.6 | | | 1.2 | 2.5 | | 0.3 | 2.1 | | | | |
| 8 | 51.8 | 18.3 | 2.5 | 2.5 | 11.7 | 7.3 | | 0.3 | 2.3 | 1.8 | 1.0 | 0.5 | | | | | |
| 9 | 52.6 | 18.5 | 1.1 | 2.5 | 11.8 | 7.3 | | 0.3 | 2.4 | 1.9 | 1.0 | 0.6 | | | | | |
| 10 | 53.0 | 18.5 | 0.6 | 2.6 | 11.8 | 7.3 | | 0.3 | 2.4 | 1.9 | 1.0 | 0.6 | | | | | |
| 11 | 53.9 | 18.9 | 1.2 | 2.6 | 12.1 | 7.5 | | 0.3 | | 1.9 | 1.0 | 0.6 | | | | | |
| 12 | 51.8 | 18.2 | 1.1 | 2.5 | 11.6 | 7.2 | | 0.2 | 2.3 | 1.8 | 1.0 | 2.3 | | | | | |
| 13 | 53.9 | 18.9 | 1.2 | 2.6 | 12.1 | 2.9 | 2.2 | 0.3 | 2.4 | 1.9 | 1.0 | 0.6 | | | | | |
| 14 | 50.3 | 16.9 | 4.2 | 5.0 | 10.8 | 8.1 | | | 2.6 | 1.6 | | 0.5 | | | | | |
| 15 | 50.6 | 15.0 | 5.2 | 11.2 | 9.0 | 6.8 | | 0.2 | 0.3 | 0.8 | | 0.9 | | | | | |
| 16 | 53.9 | 16.1 | 2.5 | 5.4 | 10.0 | 7.3 | | 0.3 | 0.3 | 0.9 | | 0.3 | 3.0 | | | | |
| 17 | 52.2 | 15.6 | 2.5 | 5.3 | 9.7 | 7.0 | | 0.2 | 0.3 | 0.9 | | 0.3 | | 3.0 | | 3.0 | |
| 18 | 55.6 | 16.6 | 2.6 | 5.6 | 10.3 | 7.5 | | 0.3 | 0.3 | 0.9 | | 0.3 | | | | | |
| 19 | 50.7 | 15.7 | 2.5 | 4.9 | 13.5 | 7.1 | | 0.2 | 2.3 | 1.8 | 1.0 | 0.3 | | | | | |
| 20 | 55.8 | 13.5 | 0.6 | 4.1 | 12.5 | 9.1 | | 0.4 | 1.2 | 2.5 | | 0.3 | | | | | |
| 21 | 54.6 | 14.4 | 0.6 | 4.1 | 13.8 | 8.1 | | 0.4 | 1.2 | 2.5 | | 0.3 | | | | | |
| 22 | 54.5 | 13.1 | 0.5 | 4.0 | 12.2 | 7.2 | | 0.4 | 1.2 | 6.5 | | 0.3 | | | | | |
| 23 | 54.0 | 13.1 | 0.6 | 4.0 | 12.1 | 6.2 | | 0.4 | 1.1 | 8.2 | | 0.3 | | | | | |
| 24 | 57.3 | 12.1 | 0.6 | 4.2 | 11.4 | 8.5 | | 0.4 | 1.2 | 2.5 | | 0.3 | 1.5 | | | | |
| 25 | 52.7 | 18.9 | 1.2 | 2.6 | 10.0 | 7.5 | | 0.3 | 1.0 | 1.9 | 0.3 | 0.6 | | | | | 3.0 |
| 26 | 54.0 | 20.7 | 1.2 | 2.6 | 10.1 | 7.3 | | 0.3 | 1.0 | 1.9 | 0.3 | 0.6 | | | | | |
| 27 | 56.2 | 14.6 | 2.7 | 5.7 | 10.5 | 7.6 | 0.6 | 0.3 | 0.3 | 0.9 | | 0.6 | | | | | |
| 28 | 54.4 | 19.1 | 1.2 | 2.6 | 9.4 | 8.9 | 0.3 | 0.3 | 1.0 | 1.9 | 0.3 | 0.6 | | | | | |
| 29 | 54.3 | 17.0 | 1.1 | 2.6 | 10.7 | 9.0 | | 0.3 | | 1.9 | 3.0 | 1.1 | | | | | |

TABLE II

| Example no. | Specimen preparation | Sintering temperature range for the prepartion of rods for α measurement | 3-point flexural strength [MPa] | Linear thermal expansion coefficient α [10⁻⁶ K⁻¹] (100–500° C.) | Tg [°C.] | Resistance to acid relative material loss [%] | Crystalline phases forming in the structure | |
|---|---|---|---|---|---|---|---|---|
| 4 Pressed ceramic | compressed in viscous state at 1050° C./10' holding time; 25' pressing time | | 209 ± 19 | 18.6 | | 0.292 | Leucite Leucite spherolites phosphosilicate needles | φ ~ 2 μm φ ~ 500 nm l ~ 1 μm φ ~ 200 nm |
| 5 Pressed ceramic | compressed in viscous state at 1100° C./10' holding time; 11' pressing time additonal intrinsic glaze tempering at 900° C./1 h | | 197 ± 13 | 19.6 | 530 | | Leucite Phosphosilicate needles | φ ~ 2–3 μm l ~ 2 μm φ ~ 200 nm |
| 9 Pressed ceramic | compressed in viscous state at 1050° C./10' holding time; 6' pressing time | | 207 ± 21 | 16.7 | 550 | 0.049 | Leucite Apatite phase | φ ~ 2–3 μm l ~ 2 μm φ ~ 100 nm |
| 9 Pressed ceramic | compressed in viscous state at 1050° C./10' holding time; 6' pressing time additional intrinsic glaze tempering at 950° C./1 h and additional ground glaze at 850° C./2' | | 334 ± 34 | | | | Leucite Apatite phase | φ ~ 2–3 μm l ~ 2 μm φ ~ 100 nm |
| 9 Sintered ceramic | granulate; tempered 1100° C./1 h ground up Powder <90 μm sieved | | | | | | Leucite Apatite phase Silicon oxide (quartz) | |
| 11 Pressed ceramic | compressed in viscous state at 1020° C./10' holding time; 6' pressing time | | | 16.6 | 550 | 0.045 | Leucite Fluorapatite needles | φ ~ 2 μm l ~ 2 μm φ ~ 100 nm |
| 7 Sintered ceramic | granualte; tempered 1000° C./30' ground up; powder <90 μm sieved | 940° C./960° C. | 154 ± 29 | 10.8 | 596 | | Leucite Small phospho-silicate rods phosphosilicate spherolites 2nd glass phase in drop form | φ ~ 80 nm l ~ 1 μm φ ~ 100 nm φ ~ 150 nm |
| 7 Sintered ceramic | Powder <90 μm tempered at 950° C./1 h ground up; powder <90 μm sieved | 940° C./960° C. | | 15.2 | | 0.017 | Leucite Small phospho-silicate rods phosphosilicate spherolites 2nd glass phase in drop form | φ <2 μm φ ~ 100 nm l ~ 1 μm φ ~ 100 nm φ ~ 150 nm |
| 18 Sintered ceramic | granulate; tempered 1000° C./1 h ground up powder <90 μm sieved | | | | | | Leucite Fluorapatite Silicon oxide (quartz) | |

Example 30

This example describes the preparation of a glass-ceramic according to the invention and the possibility of using it as a framework material for the preparation of an individually mouldable all-ceramic product, such as e.g. a crown or bridge, onto which an adapted sintered dental ceramic is additionally sintered.

Firstly, a starting glass having the chemical composition given in Table I for Example 4 was prepared. For this, a mixture of oxides, carbonates, phosphates and fluorides was melted in a platinum/rhodium crucible at a temperature of 1500° to 1640° C. during a homogenization period of an hour. The glass melt was quenched in water, and the formed glass frit was dried, ground in an Achat ball mill for 2 hours and sieved to a grain size of less than 45 μm. The obtained glass powder was then pressed by means of a uniaxial dry press at room temperature and at a pressing pressure of 1000 bar to give cylindrical green compacts with a mass of about 4 g each.

The green compacts were then sintered in vacuum in a furnace to give the glass-ceramic according to the invention in the shape of a ingot, this operation being carried out at a heat-up rate of 30° C./minute and the final temperature of 950° C. being held for 30 minutes.

The obtained ingots were finally compressed in vacuum in the viscous state into the specimen geometry desired for the test in question, using the pressing process and pressing oven according to EP-A-0 231 773. The readiness temperature of the pressing oven was 600° C., the heating rate up to the pressing temperature 60° C./min, the pressing temperature 1100° C., the holding time at the pressing temperature 10 min and the pressing pressure 8 bar. After the pressing operation, the pressing mould was cooled in air and the specimen bodies were removed from the mould by sandblasting with glass beads.

The obtained specimens were subjected to the following tests:

3-point flexural strength

For this, rods measuring 1.5×4.8×20 mm were pressed, and these were ground over on all sides with SiC wet-grinding paper (1000 grain size). The flexural strength was ascertained with a support width of the test preparation of 15 mm and a rate of advance of the load application of 0.5 mm/min. The 3-point flexural strength established under these conditions according to ISO 6872-1984 was 209±19 MPa.

After the grinding operation, a dental ceramic with adapted thermal expansion coefficient was sintered a part of the pressed rods in a manner customary in the preparation of part-crowns, crowns or bridges. After a 5-fold repetition of the baking operation, the baked-on glaze had in each case a layer thickness of ca. 20 to 30 μm. For the rods treated in this way, a flexural strength of 224±10 MPa was measured under the conditions given above.

Linear thermal expansion coefficient

Cylindrical specimens with a diameter of 6 mm and a length of 26 mm were pressed. The expansion coefficient measured in the range from 100° to 500° C. for these specimens was $18.6 \times 10^{-6} K^{-1}$.

Resistance to acid

For this, disk-shaped specimens with a diameter of 15 mm and a thickness of 1.5 mm were pressed and then ground over on all sides with SiC wet-grinding paper (1000 grain size). The relative material loss of these specimens, measured according to ISO 6872-1984, after 16 hours' storage in 4 vol.-% aqueous acetic acid solution was only 0.292% and is thus clearly below the standard value of 0.5% for dental ceramic materials.

Example 31

Just like Example 30, this example shows the preparation of a glass-ceramic according to the invention and the possibility of its use as a framework material for the preparation of an individually mouldable all-ceramic product, such as a crown or bridge.

Pressed glass-ceramic specimens having the chemical composition given in Table I for Example 9 were prepared.

The procedure described in Example 30 was chosen with the following changes:

Sintering process of the green compacts to give the glass-ceramic ingots at a final temperature of 920° C.;

Heating rate up to the pressing temperature: 60° C./min;

Pressing temperature: 1050° C.;

Pressing pressure: 5 bar.

The tests carried out according to Example 30 produced the following results:

3-point flexural strength

It was measured for various specimens:

Specimens (a): compressed without further treatment: 207±21 MPa

Specimens (b): these were subjected to a 1-hour tempering in air at 950° C. after the grinding operation and thereupon displayed an intrinsic glaze on the surface. They had a noticeably higher flexural strength of 260±21 MPa.

Specimens (c): A dental ceramic with an adapted expansion coefficient was baked onto these in the usual manner at 850° C. and with a holding time of 2 min after the grinding process. After 5-fold repetition of the baking process, the baked-on glaze had a layer thickness of ca. 20 to 30 μm. A flexural strength of 260±65 MPa was measured for the specimens treated in this way.

Specimens (d): These were obtained by tempering as in the case of the specimens (b) and subsequent baking on of a dental ceramic as in the case of the specimens (c). The sum of the layer thickness of intrinsic glaze and sintered glaze was ca. 50 μm. An excellent flexural strength of 334±34 MPa was measured for the specimens treated in this way.

Linear thermal expansion coefficient

For this, specimens were used which had not been further thermally treated, and they had an expansion coefficient of $16.7 \times 10^{-6} K^{-1}$.

Resistance to acid

For this, specimens were used which had not been further thermally treated after the pressing operation, and they displayed a relative material loss of 0.049%.

Example 32

This example describes the preparation of a glass-ceramic according to the invention which, because of its translucence, can be used as a part-crown or as a framework material for all-ceramic dental products, such as crowns or bridges.

Pressed glass-ceramic specimens having the chemical composition given in Table I for Example 11 were prepared. For this, the procedure described in Example 30 was chosen with the following changes:

Sintering process of the green compacts to give the glass ceramic blanks at a final temperature of 920° C.;

Pressing temperature: 1020° C.;

Pressing pressure: 5 bar.

The tests carried out according to Example 30 led to the following results:

3-point flexural strength

It was measured for various specimens:

Specimens (a): without further thermal treatment: 154±29 MPa

Specimens (b): these were subjected to a 1-hour tempering at 900° C. in air after the grinding operation and thereupon displayed an intrinsic glaze on the surface. They had a clearly higher flexural strength of 208±66 MPa.

Specimens (c): A dental ceramic with an adapted expansion coefficient was sintered these in the usual manner at 850°

C. and with a holding time of 2 min after the grinding process. After 5-fold repetition of the baking process, the sintered glazed had a layer thickness of ca. 20 to 30 μm. A flexural strength of 290±34 MPa was measured for the specimens treated in this way.

Linear thermal expansion coefficient

For this, specimens were used which had not been further thermally treated, and they had an expansion coefficient of $16.6 \times 10^{-6} K^{-1}$.

Resistance to acid

For this, specimens were used which had not been further thermally treated after the pressing operation, and they displayed a relative material loss of 0.045%.

Example 33

This example describes the preparation of a glass-ceramic according to the invention which is suitable for sintered onto a metal framework and can thus be used as a constituent of metal ceramic dental products, such as metal ceramic crowns or bridges.

Firstly, a starting glass having the chemical composition given in Table I for Example 7 was prepared. For this, a mixture of oxides, carbonates, phosphates and fluorides was melted in a platinum/rhodium crucible at a temperature of 1500° to 1650° C. during a homogenization period of 1 to 1.5 hours. The glass melt was quenched in water, and the formed glass granulate was dried. A part of the formed granulate was ground to give a glass powder with an average grain size of less than 90 μm.

To form glass-ceramics from the starting glass, the glass granulate was heat-treated for 0.5 hours at 1000° C. and the glass powder for 1 hour at 950° C. The glass-ceramic formed in each case was examined by means of scanning electron microscopy and the formed crystals were identified by means of X-ray diffractometry. It was possible to detect a leucite crystalline phase and a phosphate-containing crystalline phase in both glass-ceramics.

The glass-ceramics formed from the glass granulate and the glass powder were each reground and sintered to give green compacts in the shape of small rods in a vacuum oven at a heating-up rate of 60° C./min and with a holding time of 1 min at 960° to 980° C. The following thermal expansion coefficients were measured in the temperature range from 100° to 500° C. for the thus-obtained specimens and for a green compact prepared from the starting glass under identical conditions:

glass-ceramic prepared from glass granulate: $10.8 \times 10^{-6} K^{-1}$ glass-ceramic prepared from glass powder: $15.2 \times 10^{-6} K^{-1}$ starting glass: $10.7 \times 10^{-6} K^{-1}$ Through suitable mixing of these three materials, the expansion coefficient can be adjusted so that the obtained dental ceramic can be used for sintering onto a dental alloy and can thus be used for the formation of a metal ceramic dental restoration.

In analogous manner, different glass-ceramics according to the invention can be mixed with one another or with starting glasses in order to achieve desired expansion coefficients. Thus it is e.g. possible to mix the glass ceramic according to Example 7 with a starting glass of the chemical composition according to Example 24 in a ratio of 70:30% by wt., in order to obtain a glass-ceramic according to the invention with outstanding optical properties and an expansion coefficient of e.g. $13.0 \times 10^{-6} K^{-1}$. Such a glass-ceramic is excellently suitable as a sintering ceramic for a dental alloy.

Example 34

This example describes a glass-ceramic according to the invention which in powder form is transformable into a plastic state through the addition of organic plasticizing agents and can be processed by suitable moulding operations to give dental products such as artificial teeth.

Firstly, a starting glass having the chemical composition given in Table I for Example 22 was prepared. For this, a glass powder with an average grain size of less then 90 μm was prepared according to the process as per Example 33. The glass powder was then tempered for 1 hour at a temperature of 1050° C. It was possible to detect leucite crystals and phosphate-containing crystals in the glass-ceramic formed thereby.

The glass-ceramic formed from the glass powder was reground and processed to give testpieces. The expansion coefficient and the resistance to acid were then measured according to Example 32 with the following results:

expansion coefficient: $14.1 \times 10^{-6} K^{-1}$ relative material loss: 0.017%.

We claim:

1. A leucite-containing phosphosilicate glass-ceramic comprising a leucite crystalline phase and at least one further crystalline phase and at least one glass phase, and comprising the following components:

| | |
|---|---|
| $SiO_2$ | 49.0 to 57.5% by wt. |
| $Al_2O_3$ | 11.4 to 21.0% by wt. |
| $P_2O_5$ | 0.5 to 5.5% by wt. |
| CaO | 2.5 to 11.5% by wt. |
| $K_2O$ | 9.0 to 22.5% by wt. |
| $Na_2O$ | 1.0 to 9.5% by wt. |
| $Li_2O$ | 0 to 2.5% by wt. |
| $B_2O_3$ | 0 to 2.0% by wt. |
| $TiO_2$ | 0 to 3.0% by wt. |
| $ZrO_2$ | 0.8 to 8.5% by wt. |
| $CeO_2$ | 0 to 3.0% by wt. |
| F | 0.25 to 2.5% by wt. |
| $La_2O_3$ | 0 to 3.0% by wt. |
| ZnO | 0 to 3.0% by wt. |
| BaO | 0 to 3.0% by wt. |
| MgO | 0 to 3.0% by wt. |
| SrO | 0 to 3.0% by wt. |

2. The glass-ceramic according to claim 1 wherein the quantities of the components, independently of one another, are as follows:

| | |
|---|---|
| $SiO_2$ | 50 to 57% by wt. |
| $P_2O_5$ | 0.5 to 4.0% by wt. |
| CaO | 2.5 to 7.0% by wt. |
| $K_2O$ | 9.0 to 15.0% by wt. |
| $Na_2O$ | 5.0 to 9.5% by wt. |
| $Li_2O$ | 0 to 1.5% by wt. |
| $B_2O_3$ | 0 to 1.0% by wt. |
| $TiO_2$ | 0 to 2.5% by wt. |
| $ZrO_2$ | 0.8 to 5.0% by wt. |
| $La_2O_3$ | 0 to 2.0% by wt. |

3. The glass-ceramic according to claim 1, wherein the further crystalline phase is a phosphate-containing crystalline phase.

4. The glass-ceramic according to claim 3, wherein the phosphate-containing crystalline phase is an apatite crystalline phase.

5. The glass-ceramic according to claim 1, wherein the crystalline phases comprise crystals and the crystals of the phases are essentially of the same size and have an average size of less than 5 μm.

6. The glass-ceramic according to claim 1, wherein the leucite crystalline phase and the further crystalline phase comprise elongated phosphate-containing crystals.

7. The glass-ceramic according to claim 6, wherein the elongated phosphate-containing crystals are needle-shaped apatite crystals and have an average size of less than 2 μm.

8. The glass-ceramic according to claim 1 further comprising additives selected from the group consisting of dyestuffs, fluorescent substances, glasses, ceramics, glass-ceramics, opacifiers and stabilizers.

9. A process for the preparation of a glass-ceramic comprising:

(a) preparing a glass composition comprising:
49.0 to 57.5% by wt. $SiO_2$, 11.4 to 21.0% by wt. $Al_2O_3$, 0.5 to 5.5% by wt. $P_2O_5$, 2.5 to 11.5% by wt. CaO, 9.0 to 22.5% by wt. $K_2O$, 1.0 to 9.5% by wt. $Na_2O$, 0 to 2.5% by wt. $Li_2O$, 0 to 2.0% by wt. $B_2O_3$, 0 to 3.0% by wt. $TiO_2$, 0.8 to 8.5% by wt. $ZrO_2$, 0 to 3.0% by wt. $CeO_2$, 0.25 to 2.5% by wt. F, 0 to 3.0% by wt. $La_2O_3$, 0 to 3.0% by wt. ZnO, 0 to 3.0% by wt. BaO, 0 to 3.0% by wt. MgO, and 0 to 3.0% by wt. SrO;

(b) providing the glass of (a) in the form of a powder or granulate or of a green compact pressed out of powder;

(c) subjecting the powder of (b) to a heat treatment in the temperature range of from 850° C. to 1200° C. for a period of from 30 minutes to 4 hours; and (d) forming a glass-ceramic comprising a leucite crystalline phase.

10. The process according to claim 9, wherein the heat treatment is carried out for a period of 1 to 2.5 hours.

11. The process according to claim 9, wherein before the heat treatment, the formed glass is pulverized or granulated to an average particle size of less than 90 μm.

12. The process according to claim 9, further comprising:

(e) adding an additive to the formed glass-ceramic, wherein the additive is selected from the group consisting of dyestuffs, fluorescent substances, glasses, ceramics, glass-ceramics, opacifiers, and stablizers.

13. A dental product comprising the glass-ceramic of claim 1.

14. The dental product of claim 13, selected from the group consisting of crowns, bridges, part-crowns, inlays, onlays, artificial teeth, stump constructions, and facets.

15. The dental product of claim 13, wherein the dental product is an all-ceramic or metal ceramic dental product.

* * * * *